United States Patent [19]

Huber

[11] Patent Number: 5,059,812

[45] Date of Patent: Oct. 22, 1991

[54] CONTROL APPARATUS FOR CONTROLLING AN ASPIRATOR TUBE IN AN AUTOMATIC SAMPLE DISPENSER

[75] Inventor: Bernhard Huber, Überlingen, Fed. Rep. of Germany

[73] Assignee: Bodenseewerk Perkin Elmer GmbH, Überlingen, Fed. Rep. of Germany

[21] Appl. No.: 595,129

[22] Filed: Oct. 9, 1990

[30] Foreign Application Priority Data

Oct. 14, 1989 [DE] Fed. Rep. of Germany ....... 3934344

[51] Int. Cl.$^5$ ............................................. G01N 15/06
[52] U.S. Cl. ..................................... 250/577; 250/902; 73/293
[58] Field of Search ...................... 250/227.31, 227.14, 250/227.32, 573, 577, 902, 904; 73/293, 864.12, 864.24, 864.25; 340/619

[56] References Cited

U.S. PATENT DOCUMENTS

| | | | |
|---|---|---|---|
| 4,038,650 | 7/1977 | Evans et al. | 73/293 |
| 4,065,973 | 1/1978 | Gordon | 73/864.25 |
| 4,179,623 | 12/1979 | Jacobsen | 250/573 |
| 4,410,020 | 10/1983 | Lorenz | 73/293 |

FOREIGN PATENT DOCUMENTS 3235591 3/1984 Fed. Rep. of Germany .

Primary Examiner—David C. Nelms
Assistant Examiner—S. Allen
Attorney, Agent, or Firm—Thomas P. Murphy; Edwin T. Grimes

[57] ABSTRACT

The control apparatus controls the lowering motion of an aspirator tube into a sample vessel in an automatic sample dispenser in a manner such that the smallest possible portion of an external surface of the aspirator tube is wetted by a liquid present in the sample vessel. A servo drive lowers the aspirator tube into the sample vessel. A sensor arrangement containing a single light guide, a light transmitter and a photoelectric receiver is associated with the aspirator tube and responds to light reflections at the liquid surface upon immersion of the lower aspirator tube end into the liquid. The light guide guides the propagating light beam and a returning reflected light beam. An electronic control controls the advancement of the aspirator tube via the servo drive into a position in which a predetermined short length in the region of the lower aspirator tube end dips into the liquid. When the liquid level drops due to aspiration of liquid into the aspirator tube, the lower end of the latter follows just this drop of the liquid level so that the aspirator tube continuously remains immersed into the liquid but only with the short length at its lower end.

5 Claims, 4 Drawing Sheets

CONTROL APPARATUS FOR CONTROLLING AN ASPIRATOR TUBE IN AN AUTOMATIC SAMPLE DISPENSER

FIELD OF INVENTION

The present invention relates to a control apparatus for controlling a lowering motion of an aspirator tube in an automatic sample dispenser.

In its more particular aspects, the invention specifically relates to a controlling apparatus for controlling, in an automatic sample dispenser, the lowering movement of an aspirator tube into a sample vessel which is filled with a sample liquid. In such automatic sample dispenser,
(a) the aspirator tube can be lowered into the sample vessel by means of a servo drive,
(b) light guide means are provided and extend along the aspirator tube, and
(c) a light transmitter and a photoelectric light receiver are provided and light is guided by the light guide means from the light transmitter to the lower end of the aspirator tube on the side of the sample liquid, whereby the light exiting from the lower end of the aspirator tube exits in a direction toward the surface the sample liquid and light reflected at the surface of the sample liquid is guided by the light guide means to the photoelectric light receiver.

Automatic sample dispensers, so-called autosamplers serve to aspirate sample liquid from sample vessels and to feed the aspirated sample liquid to an analytical instrument, for example, an atomic absorption spectrophotometer. Such automatic sample dispensers, however, can also be employed in connection with other types of analytical instruments like, for instance, gas chromatographs, liquid chromatographs or instruments used in the field of clinical chemistry.

BACKGROUND OF THE INVENTION

From German Published Patent Application Nos. 1,934,668 and 1,944,825 there is known a dosing device for an instrument used for carrying out chemical analyses. This dosing device contains an aspirator tube for aspirating a liquid from a sample vessel and successively metering the aspirated liquid into different reaction vessels. The aspirator tube is in connection with a rinsing liquid pump. Following each aspirating and metering operation which is effected by means of a metering pump also connected to the aspirator tube, residual sample liquid is displaced from the aspirator tube by rinsing liquid which is forced into the aspirator tube by the rinsing liquid pump. As a result, the aspirator tube is completely filled with rinsing liquid at the start of each operating cycle.

U.S. Pat. No. 4,111,051 is concerned with an apparatus for dosing sample liquid taken from sample vessels into a graphite furnace for electrothermally atomizing the sample liquid in an atomic absorption spectrophotometer. This apparatus contains an aspirator tube which is connected with a metering pump as well as a rinsing liquid reservoir via a rinsing liquid pump. At the start of each operating cycle, the aspirator tube is filled with rinsing liquid. The aspirator tube is introduced into a sample vessel. A predetermined amount of rinsing liquid is aspirated from the aspirator tube by means of the metering pump and, correspondingly, a predetermined amount of sample liquid is taken up from the sample vessel. Subsequently, the aspirator tube is introduced Into the graphite furnace. The metering pump forces the sample liquid out from the aspirator tube into the graphite furnace. Thereafter, a rinsing operation is effected. For this purpose, the aspirator tube is introduced into a rinsing vessel constituting an overflow vessel. Therein the aspirator tube portions which had contacted the sample liquid, are immersed into rinsing liquid. The rinsing liquid pump delivers a preselected volume of rinsing liquid via the aspirator tube into the rinsing vessel and via the rinsing vessel into a waste container. During this operation, the aspirator tube is internally and externally rinsed. In this manner there is prevented carry-over of sample liquid when the aspirator tube is subsequently immersed into a further sample vessel for aspirating and metering the next-following sample liquid.

A similar arrangement is described in U.S. Pat. No. 4,068,529.

There are also known automatic sampler dispensers in which the aspirator tube is vertically movably guided at a carrier and can be vertically reciprocated by means of a stepping motor. The carrier is controlled for movement in a horizontal plane such as to be successively placed above different sample vessels and the inlet of an analytical instrument like, for example, a high-pressure liquid chromatograph.

In these known automatic sample dispensers the aspirator tube is immersed into the sample vessel down to a predetermined depth in each case. During standard operations, the aspirator tube is introduced down to the lowest location of the sample vessel in order to ensure immersion of the aspirator tube into the sample liquid. The aspirator tube thus is wetted by the sample liquid also externally along a relatively great length. This may result in considerable measuring errors in highly sensitive measurements such as, for example, atomic absorption spectroscopy due to sample carry-over. Such undesirable effect may occur when successively analyzing samples containing extremely high and extremely low concentrations of the element to be determined. This problem can be reduced by using the aforedescribed rinsing operation. However, such rinsing operation requires an additional period of time. Furthermore, sample carry-over may also be effected in the rinsing vessel.

Therefore, there are known means for measuring and regulating the immersion depth of a dosing tube or pipette into a liquid.

It is known to pneumatically detect the liquid surface. In such apparatus, a level sensor has an air exit opening which is restricted when the level sensor approaches the liquid surface. There is thus caused a pressure increase which serves as a control signal. Such pneumatic level sensors are described, for example, in European Published Patent Application No. 273,128 and German Patent No. 3,039,475.

It is further known to set a pipette or dosing tube into mechanical oscillations. A sensor taps the oscillation amplitudes which serve as the control signal. These oscillation amplitudes decrease once the pipette or dosing tube is immersed into the liquid because, then, the oscillations are attenuated. An example of such level sensor is described in German Patent No. 3,614,961.

Furthermore, there are known in combination with pipettes or the like, level sensors which respond to the electrical conductivity of the liquid. Examples of such arrangements are described in German Patent No.

3,219,251 and German Published Patent Application Nos. 3,839,896; 3,905,622 and 3,909,515.

In an arrangement as described, for example, in U.S. Pat. No. 4,736,638, a turntable contains an electrically conductive plate at which the sample vessels are arranged. A low frequency oscillator is connected to the plate and generates an electrical field. A detector which is connected with the dosing tube, responds to this electrical field. When the dosing tube arrives at the liquid surface, an output signal is generated and interrupts the downward movement of the dosing tube.

Also, optical level sensors are known in combination with dosing tubes or the like for detecting the surface of liquids.

A dosing tube and a detector connected therewith are described in, for example, European Published Patent Application No. 250,671. The detector contains a light transmitter and a light receiver. Optical imaging means produce a substantially V-shaped path of rays. When the image of the light transmitter is located at the surface of the liquid, reflected light impinges upon the light receiver and generates a signal.

German Patent No. 3,113,248 describes an apparatus for taking up liquids from vessels at an analytical scale by means of a dosing tube which is immersed from above into the liquid to be taken up. A bundle of optical fibers is attached to the dosing tube and serves as level sensor. The optical fibers end above the lower end of the dosing tube by an amount corresponding to the immersion depth. A first number of the optical fibers is in communication with a light transmitter and a second number of the optical fibers is in communication with a light receiver.

In a further arrangement such as shown, for example, in German Patent No. 3,149,211, a predetermined immersion depth of the dosing tube is signalled by means of a light barrier extending transverse through the sample vessel.

German Published Patent Application No. 3,619,870 relates to a reflectometer for investigating glass fibers and containing a light transmitter, a coupling fiber and a photoelectric receiver. The light which is transmitted by the light transmitter, enters the coupling fiber through the end face thereof. The reflected light is returned by the coupling fiber and is coupled out from the coupling fiber by means of a semipermeable reflector for reflection to the photoelectric receiver.

SUMMARY OF THE INVENTION

It is one object to be achieved by the invention to provide a new and improved construction of a control apparatus for controlling an aspirator tube in an automatic sample dispenser and which control apparatus permits significantly reducing the danger of sample carry-over in automatic sample dispensers.

A further significant object to be achieved by the invention aims at providing a new and improved construction of a control apparatus for controlling an aspirator tube in an automatic sample dispenser and which control apparatus requires less time for carrying out the aspirating and dispensing operation and thereby enables increased analysis frequencies.

Still another important object to be achieved by the invention is directed to a new and improved construction of a control apparatus for controlling an aspirator tube in an automatic sample dispenser and which control apparatus is equipped with a level sensor of the simplest possible construction.

According to the present invention, these and other objects are achieved In a control apparatus of the initially mentioned type by providing, as the light guide means, a single light guide into which there is coupled in the light which is transmitted by the light transmitter, in a direction towards the lower end of the aspirator tube and from which there is coupled out the light which is reflected at the surface of the sample liquid and returned from the lower end of the aspirator tube in a direction towards the photoelectric receiver.

Thus, the aspirator tube is not introduced into the sample vessel to reach a fix ed predetermined depth. In fact, the aspirator tube is moved into the sample vessel only to the extent required to reach, in the sample liquid, a predetermined small immersion depth which is just sufficient to ensure trouble-free aspiration of the sample liquid. As a consequence, only a very small portion of the external surface of the aspirator tube contacts the sample liquid. Correspondingly less amounts of sample liquid remain adhered to the external surface of the aspirator tube. This reduces the danger of sample carry-over. Under certain conditions, there can even be dispensed with at least part of the rinsing operations such that a rinsing step is provided only after a plurality of analyses.

A number of different advantages result from the use of a single light guide for guiding the advancing or radiated light beam as well as the returning or reflected light beam:

The arrangment containing the aspirator tube and the single light guide is rendered significantly narrower as compared to prior art arrangements which contain a ring of light guides and wherein separate light guides are provided for the advancing or radiated light and the returned or reflected light. This is highly important when the aspirator tube, either for taking up or delivering a sample, must be Introduced Into narrow vessels or through narrow openings like, for example, the infeed opening of a graphite furnace for electrothermal sample atomization.

Also, in certain cases the aspirator tube may be required to be inserted deeper Into a sample vessel than normally necessary, for instance, for penetrating a surface layer and aspirating the sample from a region located below this surface layer. In such case each additional light guide increases the danger that sample liquid settles between the aspirator tube and the light guide and results in carry-over of sample liquid. Therefore, the presence of only a single light guide in the sensor arrangement is considered much more favourable.

BRIEF DESCRIPTION OF THE DRAWINGS

The invention will be better understood when consideration is given to the following detailed description thereof. Such description makes reference to the annexed drawings wherein the same or analogous components are designated by the same reference characters and wherein.

DETAILED DESCRIPTION OF THE PREFERRED EMBODIMENTS

Figure 1:
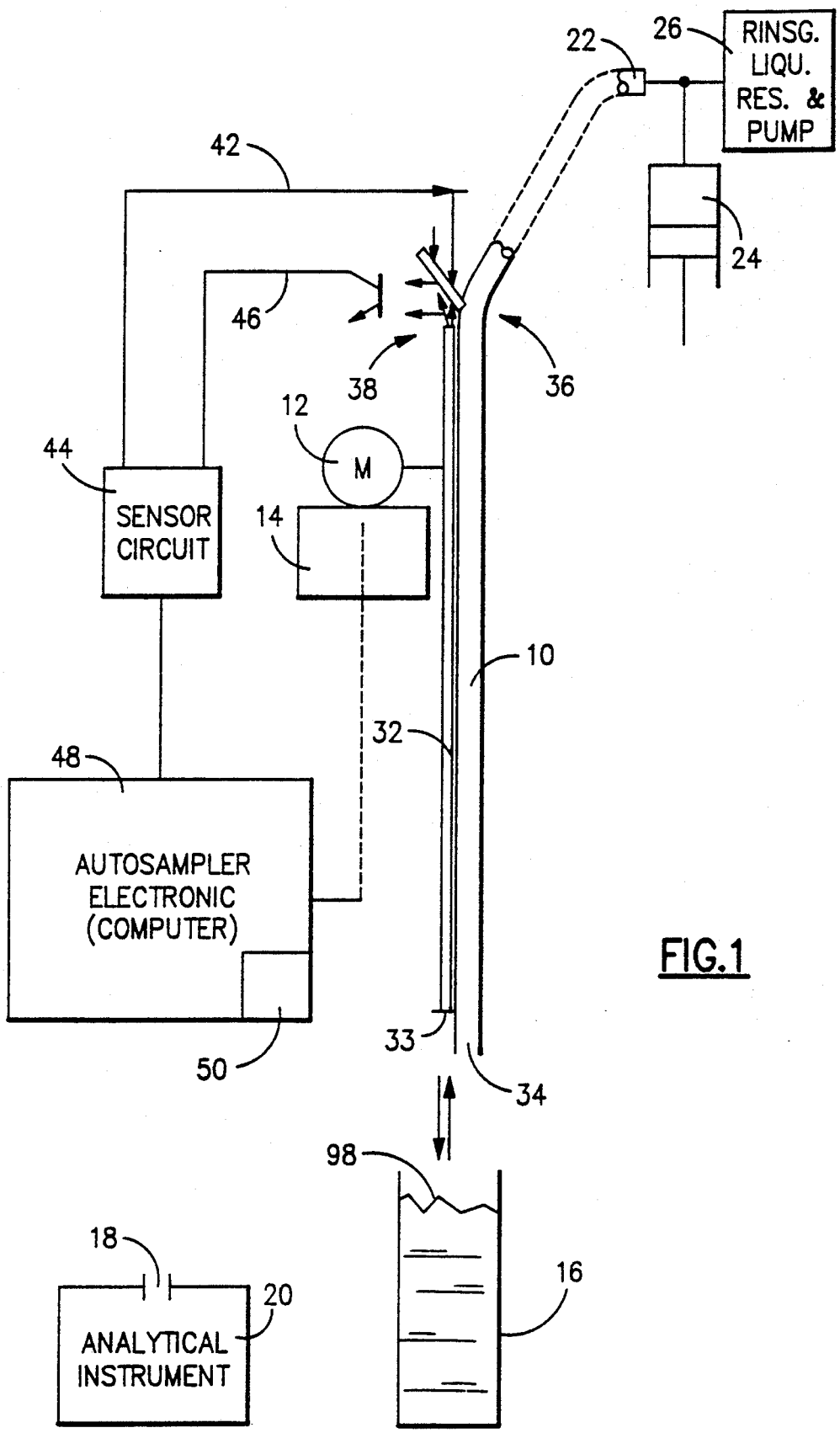
FIG. 1 is a schematic illustration showing an exemplary embodiment of the inventive control apparatus, specifically an aspirator tube in association with a sample vessel and a sensor arrangement with the associated control means.
Figure 2:
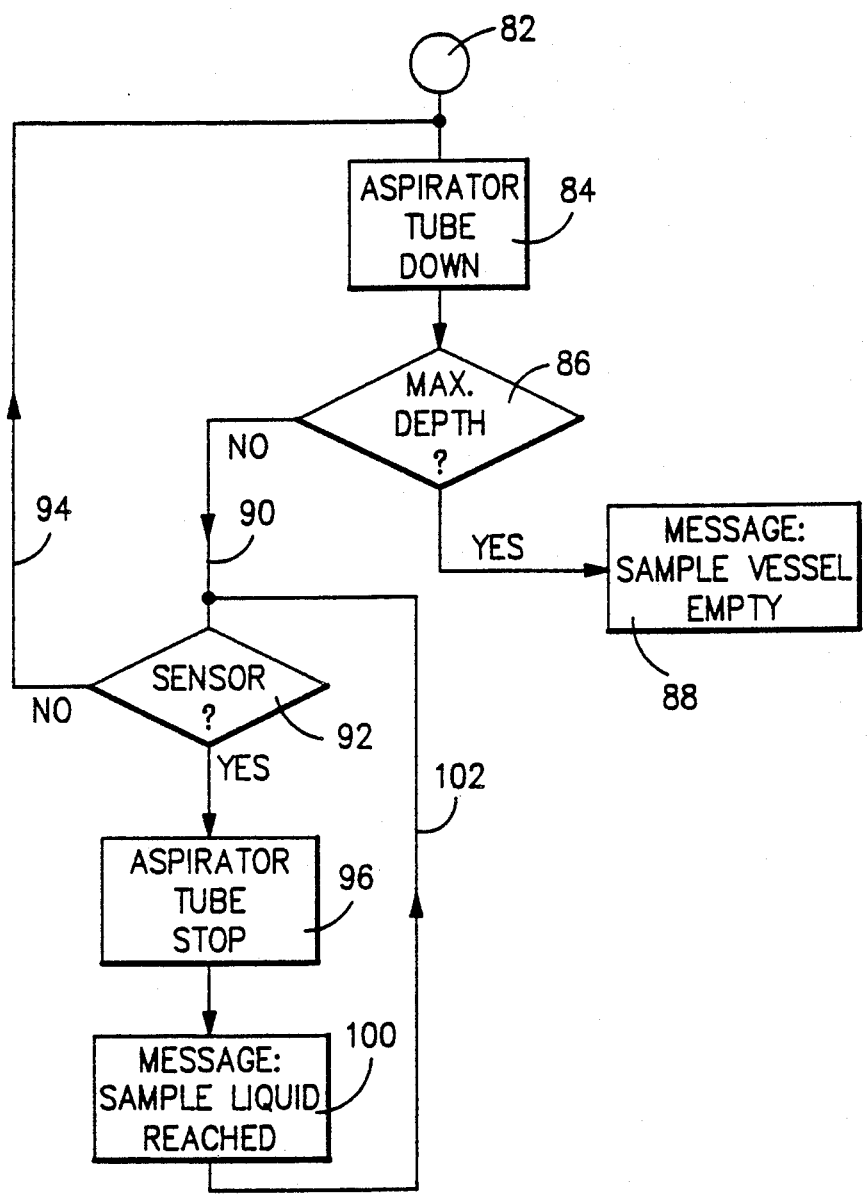
FIG. 2 is a flow diagram explaining the control of the aspirator tube as a function of the signals of the sensor arrangement.

Describing now the drawings, there is specifically shown in FIGS. 1 and 2 as a matter of example and not imitation, an exemplary embodiment of the inventive control apparatus containing an aspirator tube 10 which can be vertically reciprocated by means of a servo drive herein constituting a stepping motor 12. The stepping motor 12 is placed at a carrier or support 14 which is controlledly displaceable within a horizontal plane, i.e. a plane extending perpendicular to the plane of the drawing of FIG. 1. In this manner, the aspirator tube 10 can moved to be placed above a sample vessel 16 or above an inlet or infeed opening 18 of an analytical instrument 20 as the case may be.

The aspirator tube 10 is connected to a sample pump 24 via a flexible hose connection 22 as well as further connected to a rinsing liquid reservoir and a rinsing liquid pump which are conjointly represented in FIG. 1 by a block 26. The aspirator tube 10 is filled with a rinsing liquid at the start of an operating cycle. A small volume of air may optionally be aspirated and separates the rinsing liquid and the sample liquid.

The aspirator tube 10 is guided for placement above the sample vessel or receptacle 16 and, then, is lowered into such sample vessel or receptacle 16 by means of the stepping motor 12. During this operation, the aspirator tube 10 is immersed into the sample liquid. The sample pump 24 is energized and takes or sucks in a predetermined amount or volume of the rinsing liquid. In correspondence therewith, a corresponding predetermined amount or volume of sample liquid is sucked into the lower end of the aspirator tube 10 from the sample vessel 16.

Thereafter, the aspirator tube 10 is conveyed and placed above the inlet or infeed opening 18 of the analytical instrument 20 and lowered into the inlet or infeed opening 18. Upon energization, the sample pump 24 now forces a rinsing liquid volume which corresponds to the precedingly aspirated volume of sample liquid, into the aspirator tube 10. The aspirated volume of sample liquid is thereby discharged into the analytical instrument 20 which may constitute, for example, an atomic absorption spectrophotometer containing a graphite furnace for electrothermal atomization of the sample. In such event, the sample liquid is discharged or infed into the graphite furnace.

The foregoing description substantially corresponds to the known construction and operation of an automatic sample dispenser or auto-sampler and, therefore, will not be described herein in any further detail.

In the illustrated exemplary embodiment, it is one intended objective that the aspirator tube 10 is immersed into the sample liquid present in the sample vessel 16 only along a predeterminate small length. For this purpose, there are provided at the aspirator tube 10 sensing means which respond to the immersion of the aspirator tube 10 into the sample liquid in the sample vessel 16. These sensing means contain a light transmitter 28 and a light or photoelectric receiver 30 which are both arranged at an upper end 36 of the aspirator tube 10. A light guide constituting an optical fiber 32 is guided along the aspirator tube 10 from the light transmitter 28 to the lower end 34 of the aspirator tube 10. The light guide or optical fiber 32 ends in a light guide end 33 at a predetermined short distance above the lower end 34 of the aspirator tube 10. The light transmitter 28 is located at a predeterminate distance from and facing an upper end face of the light guide 32. Ligth coupling means 38 constituting a semitransparent mirror is inclined at an angle of 45° relative to the axis of the light guide 32 between the light transmitter 28 and the aforementioned end face of the light guide 31. A light beam issuing from the light transmitter 28 impinges upon the end face of the light guide 32 through the semitransparant mirror 38 and is passed to the lower end 33 of the light guide 32. A reflected light beam which is reflected into the light guide 32 at the lower end 33 thereof, exits from the upper end face of the light guide 32 and is directed to the laterally arranged photoelectric receiver 30 by means of the semitransparent mirror 38.

The light transmitter 28 is connected to a sensor circuit 44 by means of a flexible electric line or conductor 42. Likewise the photoelectric receiver 30 is connected to the sensor circuit 44 by means of a flexible electric line or conductor 46. The output signal of the sensor circuit 44 is applied to electronic control means 48 containing a computer.

The sensor circuit 44 will be described in detail further hereinbelow with reference to FIG. 3.

The mode of operation of the electronic control means 48 is illustrated in FIG. 2 by means of a flow diagram.

A circle 82 marks the start of the program or programmed operation. Then, the aspirator tube 10 is lowered by a predetermined distance by means of the stepping motor 12 as indicated by the block 84. Following this step, a test is made as to whether the maximum permissible depth has been reached during this step, i.e. whether the aspirator tube 10 is located closely above the base of the sample vessel 16. This test is represented by the rhombus 86 in the flow diagram of FIG. 2. In the event of a positive result of this test, the maximum depth has been reached and there is then generated a message "Empty Sample Vessel" as represented by the block 88. The aspirator tube 10 thereafter is withdrawn from the sample vessel 16 and can be guided to a further sample vessel. In the event of a negative result of the test, the flow diagram leads through a branch 90 to a further test, in particular to the test of whether the sensor has responded. This test implies examining whether the signal which is present at the output 80 of the sensor circuit 44 signals a predetermined level of light returning via the light guide 32. This test is represented by the rhombus 92 in the flow diagram of FIG. 2. In the event of a negative result of this test, the flow diagram leads back to the block or rectangle 84 via a loop 94. There is thus initiated a further downward step in the lowering movement of the aspirator tube 10.

In the event of a positive result cf the test represented by the rhombus 92, the downward drive of the aspirator tube 10 under the action of the stepping motor 12 is stopped. This is indicated by the block or rectangle 96. Furthermore, there is generated a message signaling that the surface 98 of the sample liquid has been reached at a predetermined depth. This is represented by the block or rectangle 100. Subsequently, the flow diagram leads back via a loop 102 to the input side of the rhombus 92, i.e. to the test as to whether the sensor has responded or not.

With reference to the aforenoted depth, an "intelligent" analyzing system would be able to recognize whether the liquid concerned constitutes, for example, a sample, a standard or a blank. Thus, for instance, sample vessels could be filled only up to a quarter and the analyzing system would thereby recognize this filling level as indicating the presence of the sample liquid and not a standard solution.

There is, then and under the control of the electronic control means 48, initiated in non-illustrated manner the aspirating operation by means of the sample pumpe 24. Consequently, the surface 98 of the sample liquid drops since sample liquid is sucked out from the sample vessel 16. In the event that the surface 98 of the sample liquid drops to such an extent that the sensor no longer responds, a further lowering motion of the aspirator tube 10 is started via the loop 94 and the block or rectangle 84 of the flow diagram of FIG. 2. As a result, the aspirator tube 10 is made to follow the dropping movement of the surface 98 of the sample liquid.

In this manner, the aspirator tube 10 is lowered by means of the stepping motor 12 until the light which is passed from the light transmitter 28 to the surface 98 of the sample liquid via the light guide 32 and which is reflected at the surface 98, produces via the light guide 32 at the photoelectric receiver 30 a signal such that the sensor circuit 44 responds. The stepping motor 12 is, then, turned off by the electronic control means 48. This response of the photoelectric receiver 30 and the sensor circuit 44 is only effected when the lower light guide end 33 approaches the surface 98 of the sample liquid to an extent such that the aspirator tube section including the lower end 34 and extending below the lower light guide end 33, is ensured to be immersed into the sample liquid. However, the control is carried out in a manner such that the aspirator tube 10 is not immersed into the sample liquid any further so that only a small portion of the external surface of the aspirator tube 10 is wetted by the sample liquid. As a result, the problems related to cleaning of the aspirator tube 10 and the danger of sample carry-over are significantly reduced.

Figure 3:
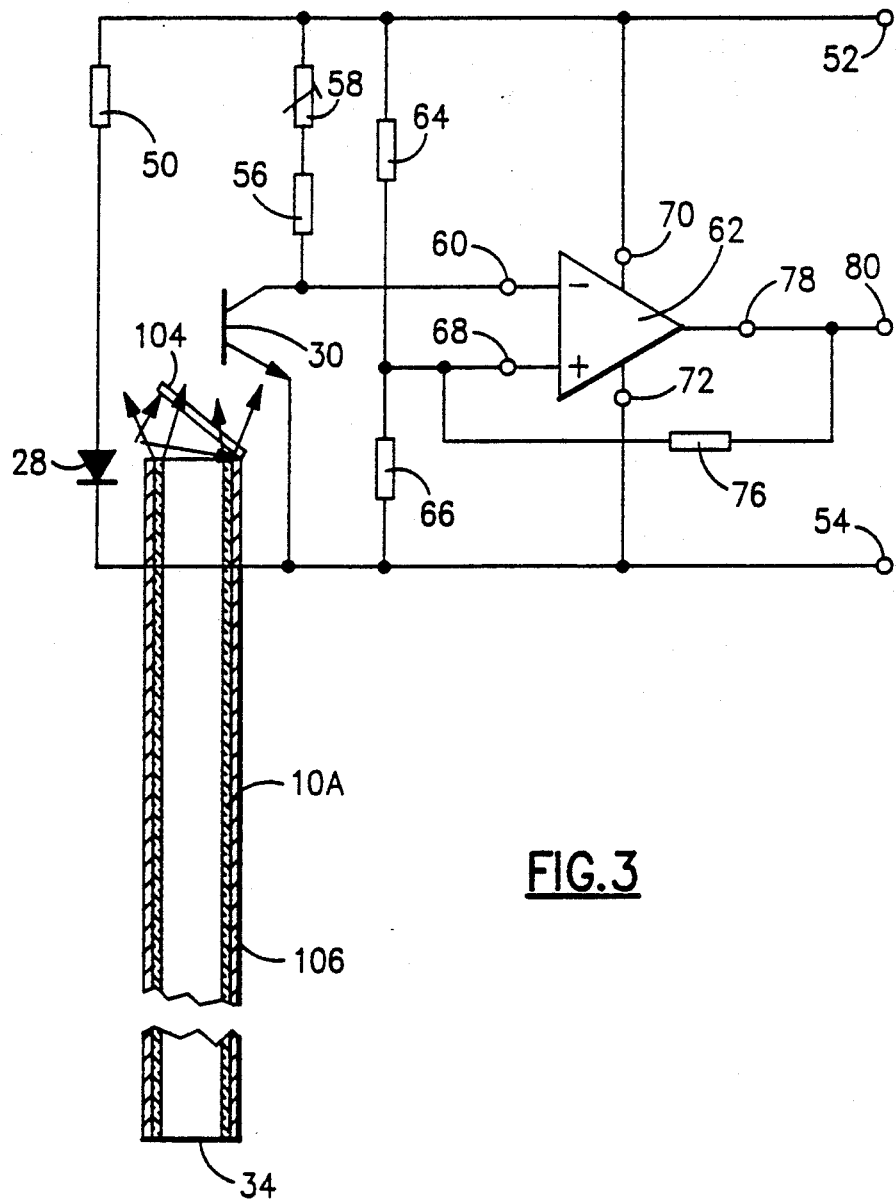
FIG. 3 is a schematic illustration of a modified exemplary embodiment in which the aspirator tube as such constitutes the light guide means.

In the modification of the exemplary embodiment illustrated in FIG. 3, the aspirator tube 10A as such serves as the light guide means constituting the single light guide through which the light emitted by the light transmitter 28 is guided to the lower end 34 of the aspirator tube 10A as well as the light reflected at the surface 98 of the sample liquid is guided towards the photoelectric detector 30. For this purpose, the aspirator tube 10A is made of a transparent material. The aspirator tube 10A is surrounded by a shell 106 which is made of a material having a lower index of refraction than the transparent material of the aspirator tube 10A. Furthermore the strength of the aspirator tube 10A is thereby increased. A semitransparent mirror 104 is provided for coupling in and out light into and from the aspirator tube 10A.

The sensor circuit 44 is also illustrated in detail in FIG. 3. The light transmitter 28 constitutes a light emitting diode (LED) which is supplied with a d.c. supply voltage through a resistor 50. The d.c. supply voltage is applied via terminals 52 and 54. The photoelectric receiver 30 constitutes a phototransistor which is impinged upon by the reflected light guided back through the single light guide, i.e. the aspirator tube 10A. The phototransistor is also connected to the d.c. supply voltage through collector resistors 56 and 58. For purposes of adjustment the resistor 58 is constructed as an adjustable resistor.

The collector voltage of the phototransistor is applied to the inverting input terminal 60 of an operational amplifier 62. A reference voltage is tapped off from a voltage divider containing the two resistors 64 and 66. This reference voltage is applied to a non-inverting input terminal 68 of the operational amplifier 62. The voltage divider 64, 66 is likewise connected to the d.c. supply voltage. The operational amplifier 62 is also powered by the d.c. supply voltage via terminals 70 and 72. A negative feedback resistor is designated by reference character 76 and is connected in circuit with a negative feedback loop leading from an output 78 of the operational amplifier 62 to the non-inverting input terminal 68 thereof.

The output or output terminal 78 of the operational amplifier 62 constitutes an output of the sensor circuit 44 and an output signal is tapped off at an output terminal 80. This output signal may assume one of two states or conditions depending upon whether the light intensity guided back to the photoelectric receiver 30 exceeds a predetermined threshold value or stays therebelow. As a function thereof, the signal voltage which is present at the inverting input terminal 60 of the operational amplifier 62, is either greater or smaller than the reference voltage applied to the non-inverting input terminal 68 of the operational amplifier 62. The output signal present at the output terminal 80 is applied to electronic control means 48 which controls the vertical reciprocating motion of the aspirator tube 10A substantially in the same manner as described hereinbefore with reference to FIG. 1 via a servo drive which is not specifically illustrated in FIG. 3.

Figure 4:
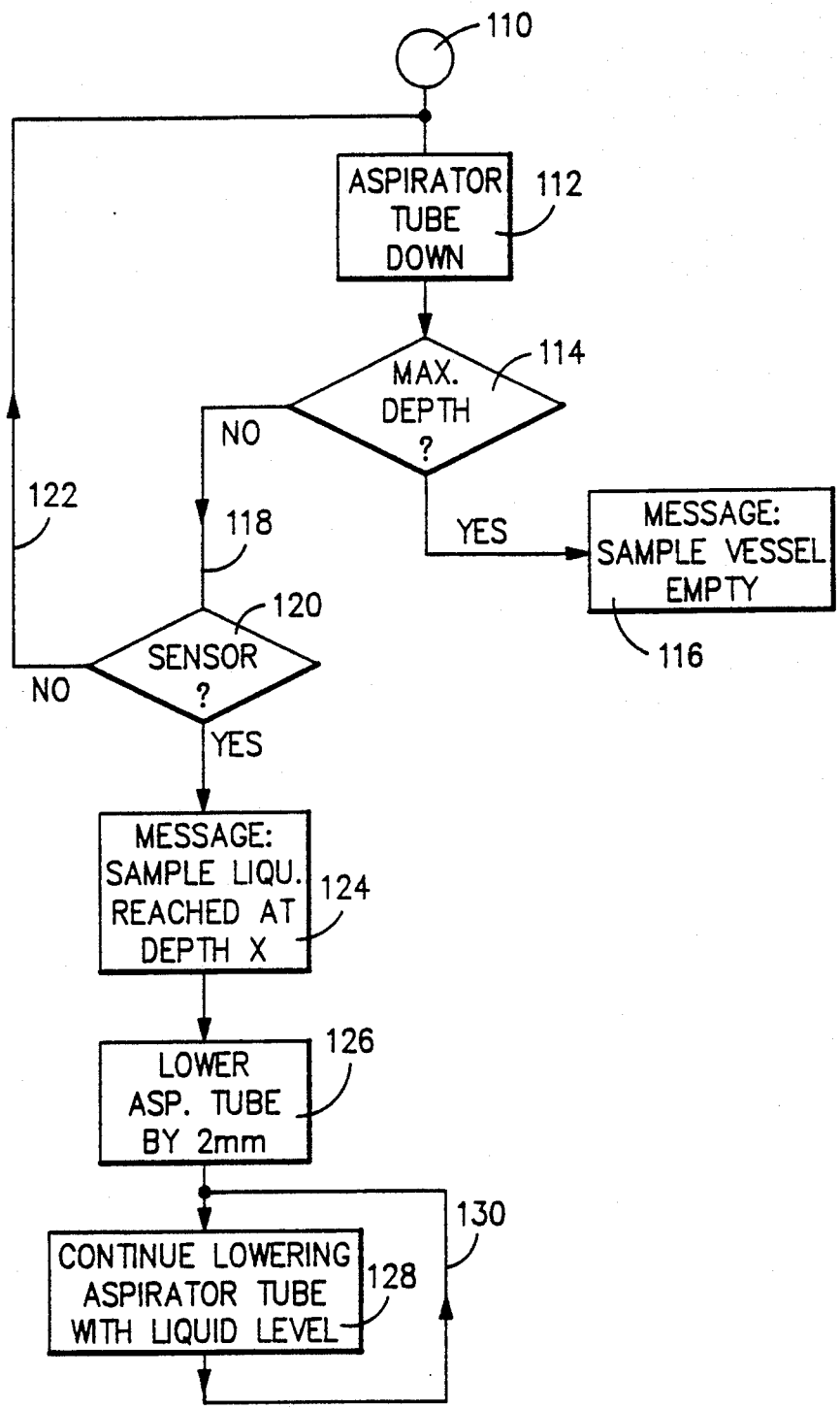
FIG. 4 is a flow diagram similar to FIG. 2 and explains the modified embodiment shown in FIG. 3.

In FIG. 4 there is illustrated a flow diagram explaining the mode of operation of the electronic control means in the modified exemplary embodiment of the inventive control apparatus as shown In FIG. 3. Since the aspirator tube 10A as such constitutes the single light guide, the end of the light guide cannot be rearwardly offset relative to the lower end of the aspirator tube in order to attain a defined immersion depth of the lower end of the aspirator tube into the sample liquid by an amount which is determined by the rearward offset of the lower light guide end. The defined immersion depth is realized by means of an appropriate control program which will become apparent from the flow diagram illustrated in FIG. 4.

A circle 110 marks the start of the program or programmed operation. Then, the aspirator tube 10A is lowered by a predetermined distance by means of the stepping motor 12 as indicated by the block 112. Following this step, a test is made as to whether the maximum permissible depth has been reached during this step, i.e. whether the aspirator tube 10A is located closely above the base of the sample vessel 16. This test is represented by the rhombus 114 in the flow diagram of FIG. 4. In the event of a positive result of this test, the maximum depth has been reached and there is then generated a message "Empty Sample Vessel" as represented by the block 116. The aspirator tube 10A thereafter is withdrawn from the sample vessel 16 and can be guided to a further sample vessel. In the event of a negative result of the test, the flow diagram leads through a branch 118 to a further test, in particular to the test of whether the sensor has responded. This test implies examining whether the signal which is present at the output 80 of the sensor circuit 44 signals a predetermined level of light returning via the light guide formed by the aspirator tube 10A. This test is represented by the rhombus 120 in the flow diagram of FIG. 4. In the event of a negative result of this test, the flow diagram leads back to the block or rectangle 112 via a loop 122. There is thus initiated a further downward step in the lowering movement of the aspirator tube 10A. So far, the control program or programmed operation illustrated by the flow diagram of FIG. 4 substantially conforms to the control program or programmed operation illustrated by the flow diagram of FIG. 2.

According to the flow diagram of FIG. 4 and as illustrated by the block or rectangle 124, there is now generated a message signalling that the sample liquid has been reached at a certain immersion depth of the aspirator tube 10A into the sample vessel 16. Subsequently, the aspirator tube 10A is further lowered by a predetermined distance such as, for example, 2 mm. It is then ensured that the lower end 34 of the aspirator tube 10A is indeed immersed into the sample liquid. This further lowering of the aspirator tube 10A is illustrated in the flow diagram of FIG. 4 by the block or rectangle 126. The rate of lowering of the liquid level is known. This rate results from the stroke rate of the sample pump 24 which conventionally is driven by a stepping motor as shown in FIG. 1, and the ratio of the cross-sectional areas of the sample pump 24 and the sample vessel 16. The further continuous lowering of the aspirator tube 10A, therefore, can be carried as a function of the stroke of the sample pump 24. This is illustrated in the flow diagram of FIG. 4 by the block 124 and the loop 130.

A conclusion concerning the residual volume of sample liquid which is present in the sample vessel 16, can be drawn from the message that the aspirator tube 10A has arrived at the sample liquid level or surface 98 at a certain immersion depth into the sample vessel 16. It is thereby possible recognizing whether the commanded or required amount of sample liquid can still be removed from the sample vessel 16.

It is further possible selecting the immersion depth signalled during the first introduction and the program step indicated by the block or rectangle 124 upon arrival at the liquid level or surface 98, as a criterion as to whether the liquid constitutes a standard solution or an unknown sample to be investigated. Thus the sample vessel 16 may be filled only to about one third when charging the sample vessel, for instance, with sample liquid to be investigated, and may be totally filled when the liquid constitutes a standard solution. Therefore, when the sensor arrangement senses a completely filled sample vessel during the first introduction of the aspirator tube 10A, the instrument "knows" that the liquid present therein constitutes a standard solution. The related position is marked In that sense in a storage or memory 50 of the electronic control means 48. Consequently, the instrument will identify liquid from this sample vessel as standard solution also at a later time when the liquid level or surface therein has subsequently dropped to a much lower height due to the removal of standard solution from this sample vessel. It is, then, no longer required to input the positions of the sample liquids to be investigated and standard solutions via a keyboard which may lead to errors.

At the present time, the aforedescribed control apparatus using a sensor which is responsive to reflections at the level or surface of the liquid present in the sample vessel, appears to represent an optimum problem solution. It has been found that these reflections are sufficient for the aforenoted purposes irrespective of the type of liquid under investigation.

Although certain particular embodiments of the invention are herein disclosed for purposes of explanation, further modification thereof, after study of this specification, will be apparent to those skilled in the art to which the invention pertains. Reference should accordingly be had to the appended claims in determining the scope of the invention:

What is claimed is:

1. A control apparatus for controlling a lowering motion of an aspirator tube into a sample vessel in an automatic sample dispenser, comprising:
    servo drive means drivingly connected to the aspirator tube for lowering said aspirator tube into a sample vessel;
    light guide means associated with and extending in the lengthwise direction of said aspirator tube;
    said aspirator tube containing a lower end facing the surface of a liquid present in said sample vessel upon lowering said aspirator tube into said sample vessel;
    a light transmitter associated with said light guide means;
    said light guide means receiving light emitted by said light transmitter and guiding said light to said lower end of said aspirator tube facing said surface of the liquid present in said sample vessel;
    said light guide means emitting said light guided to said lower end of said aspirator tube, in a direction toward said surface of the liquid present in said sample vessel;
    a photoelectric receiver associated with said light guide means;
    said light guide means receiving light reflected at said surface of the liquid present in said sample vessel and guiding said reflected light to said photoelectric receiver;
    said light guide means constituting a single light guide;
    light coupling means associated with said single light guide;
    said light coupling means coupling in light emitted by said light transmitter into said single light guide in a direction toward said lower end of said aspirator tube; and
    said light coupling means coupling out light reflected at said surface of the liquid present in said sample vessel and travelling back from said lower end of said aspirator tube, from said single light guide in a direction toward said photoelectric receiver.

2. The control apparatus as defined in claim 1, further including:
    a sensor circuit;
    flexible electrical conductors respectively connecting said light transmitter and said photoelectric receiver with said sensor circuit;
    said aspirator tube defining an upper end; and
    said light transmitter and said photoelectric receiver being arranged at said upper end of said aspirator tube.

3. The control apparatus as defined in claim 1, wherein:
    said light coupling means comprise a semitransparent mirror.

4. The control apparatus as defined in claim 1, wherein:

said aspirator tube constitutes said single light guide.

5. The control apparatus as defined in claim 1, further including:

a sensor circuit connected to said light transmitter and said photoelectric receiver associated with said single light guide;

electronic control means connected to said sensor circuit and generating a displacement signal indicative of the displacement of said aspirator tube until arrival of said lower end of said aspirator tube at said surface of the liquid present in said sample vessel;

said electronic control means classifying said displacement signal generated upon first arrival at and first immersion into said liquid present in said sample vessel, in different classes of extent of said displacement of said aspirator tube and associating said different classes of said displacement signal with different types of said liquid present in said sample vessel;

a plurality of sample vessels constituting said sample vessel;

storage means associated with said electronic control means for storing signals representative of said different classes of extent of said displacement and associated with individual ones of said plurality of sample vessels; and an analytical instrument for determining measured values associated with individual ones of said plurality of sample vessels; and said analytical instrument being operatively connected with said storage means for associating said measuring values with individual ones of said different types of liquids during successive sample aspirations from respective ones of said plurality of sample vessels.

* * * * *